US010653455B2

(12) United States Patent
Lehman, Jr. et al.

(10) Patent No.: US 10,653,455 B2
(45) Date of Patent: May 19, 2020

(54) SPINAL IMPLANT SYSTEM AND METHODS OF USE

(71) Applicant: Warsaw Orthopedic, Inc, Warsaw, IN (US)

(72) Inventors: Ronald A. Lehman, Jr., Tenafly, NJ (US); Rodney Ray Ballard, Lakeland, TN (US); William Alan Rezach, Covington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 116 days.

(21) Appl. No.: 15/702,500

(22) Filed: Sep. 12, 2017

(65) Prior Publication Data

US 2019/0076170 A1    Mar. 14, 2019

(51) Int. Cl.
*A61B 17/70* (2006.01)
*A61B 17/86* (2006.01)

(52) U.S. Cl.
CPC ...... *A61B 17/7038* (2013.01); *A61B 17/7032* (2013.01); *A61B 17/7037* (2013.01); *A61B 17/7041* (2013.01); *A61B 17/7044* (2013.01); *A61B 17/7083* (2013.01); *A61B 17/7082* (2013.01); *A61B 17/8685* (2013.01)

(58) Field of Classification Search
CPC ........ A61B 17/86–862; A61B 17/8645; A61B 17/7035–7046; A61B 17/8685
See application file for complete search history.

(56) References Cited

U.S. PATENT DOCUMENTS

| 5,207,678 | A | 5/1993 | Harms et al. |
| 5,575,792 | A | 11/1996 | Errico et al. |
| 5,609,593 | A | 3/1997 | Errico et al. |
| 5,609,654 | A | 3/1997 | Le et al. |
| 5,630,817 | A | 5/1997 | Rokegem et al. |
| 5,643,263 | A | 7/1997 | Simonson |
| 5,683,391 | A * | 11/1997 | Boyd ................. A61B 17/1637 606/264 |
| 5,797,911 | A | 8/1998 | Sherman et al. |
| 5,885,285 | A | 3/1999 | Simonson |
| 5,947,967 | A | 9/1999 | Baker |
| 6,074,391 | A | 6/2000 | Metz-Stavenhagen et al. |
| 6,280,442 | B1 * | 8/2001 | Barker ............... A61B 17/7037 606/256 |
| 6,520,962 | B1 | 2/2003 | Taylor |
| 6,562,038 | B1 | 5/2003 | Morrison |
| 6,572,618 | B1 | 6/2003 | Morrison |
| 6,579,292 | B2 | 6/2003 | Taylor |
| 6,648,887 | B2 | 11/2003 | Ashman |
| 6,685,705 | B1 | 2/2004 | Taylor |
| 6,755,830 | B2 | 6/2004 | Minfedw et al. |

(Continued)

FOREIGN PATENT DOCUMENTS

FR      2827757 A1    7/2001
JP    2001252283 A    9/2001

*Primary Examiner* — Jacqueline T Johanas
*Assistant Examiner* — Michelle C Eckman (57) ABSTRACT

A bone fastener comprises a first member defining an implant cavity. A part is connectable with the first member. A second member is configured to penetrate tissue and includes a mating surface engageable with the part. The part is engageable to selectively translate the implant cavity relative to the second member. Implants, spinal constructs, systems, instruments and methods are disclosed.

18 Claims, 10 Drawing Sheets

(56) References Cited

U.S. PATENT DOCUMENTS

| | | |
|---|---|---|
| 6,872,209 B2 | 3/2005 | Morrison |
| 7,066,939 B2 | 6/2006 | Taylor |
| 8,585,741 B2 | 11/2013 | Gabellberger et al. |
| 8,992,575 B1 | 3/2015 | Di Lauro et al. |
| 9,089,371 B1* | 7/2015 | Faulhaber .......... A61B 17/7035 |
| 9,314,274 B2 | 4/2016 | Amstutz et al. |
| 9,402,663 B2 | 8/2016 | Peterson et al. |
| 9,956,003 B2* | 5/2018 | Prevost ............. A61B 17/7035 |
| 2005/0159750 A1 | 7/2005 | Doherty |
| 2005/0273101 A1* | 12/2005 | Schumacher ...... A61B 17/7037 |
| | | 606/306 |
| 2006/0041261 A1* | 2/2006 | Osypka ............. A61B 17/8685 |
| | | 606/308 |
| 2006/0241593 A1* | 10/2006 | Sherman ........... A61B 17/7032 |
| | | 606/278 |
| 2008/0015596 A1* | 1/2008 | Whipple ........... A61B 17/7037 |
| | | 606/86 A |
| 2008/0147126 A1* | 6/2008 | Tipirneni ............... A61B 17/68 |
| | | 606/300 |
| 2010/0249846 A1* | 9/2010 | Simonson ......... A61B 17/7037 |
| | | 606/264 |
| 2011/0077693 A1* | 3/2011 | Yu ....................... A61B 17/861 |
| | | 606/305 |
| 2011/0270321 A1* | 11/2011 | Prevost ............. A61B 17/7002 |
| | | 606/305 |
| 2011/0301650 A1* | 12/2011 | Johnson ............ A61B 17/7032 |
| | | 606/305 |
| 2012/0123481 A1* | 5/2012 | Lin .................... A61B 17/7032 |
| | | 606/279 |
| 2012/0215263 A1* | 8/2012 | Lee ................... A61B 17/7037 |
| | | 606/305 |
| 2012/0253398 A1* | 10/2012 | Metcalf ............. A61B 17/7037 |
| | | 606/264 |
| 2013/0261671 A1* | 10/2013 | Horvath ............ A61B 17/8685 |
| | | 606/282 |
| 2014/0142639 A1* | 5/2014 | Vennard ........... A61B 17/8685 |
| | | 606/291 |
| 2014/0172027 A1* | 6/2014 | Biedermann ........ A61B 17/866 |
| | | 606/326 |
| 2014/0257411 A1* | 9/2014 | Rezach ............. A61B 17/7037 |
| | | 606/305 |
| 2015/0201972 A1* | 7/2015 | Doubler ............ A61B 17/7002 |
| | | 606/266 |
| 2015/0359575 A1* | 12/2015 | Pech ................... A61B 17/805 |
| | | 606/291 |
| 2016/0278815 A1* | 9/2016 | Fitzpatrick .......... A61F 2/30942 |
| 2016/0317206 A1* | 11/2016 | Rezach ............. A61B 17/7037 |
| 2017/0119537 A1* | 5/2017 | Tepper .................... A61F 2/447 |
| 2017/0245898 A1* | 8/2017 | May .................. A61B 17/7037 |
| 2018/0049777 A1* | 2/2018 | Rezach ............. A61B 17/7034 |
| 2018/0071000 A1* | 3/2018 | Pham ............... A61B 17/8685 |
| 2018/0110548 A1* | 4/2018 | May .................. A61B 17/7037 |
| 2018/0153600 A1* | 6/2018 | Koller ............... A61B 17/8625 |
| 2018/0193062 A1* | 7/2018 | May .................. A61B 17/7035 |
| 2018/0193063 A1* | 7/2018 | May .................. A61B 17/7037 |
| 2018/0206890 A1* | 7/2018 | Rezach ............. A61B 17/7032 |
| 2019/0076170 A1* | 3/2019 | Lehman, Jr. ...... A61B 17/7038 |
| 2019/0159820 A1* | 5/2019 | Geist ................. A61B 17/8685 |

* cited by examiner

SPINAL IMPLANT SYSTEM AND METHODS OF USE

TECHNICAL FIELD

The present disclosure generally relates to medical devices for the treatment of spinal disorders, and more particularly to a surgical implant system including a bone fastener and a related method.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a bone fastener is provided. The bone fastener comprises a first member defining an implant cavity. A part is connectable with the first member. A second member is configured to penetrate tissue and includes a mating surface engageable with the part. The part is engageable to selectively translate the implant cavity relative to the second member. In some embodiments, implants, spinal constructs, systems, instruments and methods are disclosed.

In one embodiment, a method of treating a spine is provided. The method comprises the steps of: reducing a spinal rod with a receiver of a bone screw that includes a part connectable with the receiver and a screw shaft engageable with the part; and engaging the part such that the receiver and the screw shaft expand to adjust position of the receiver relative to tissue.

In one embodiment, the bone fastener comprises a first member defining an implant cavity. A part is connectable to the first member. A second member is configured to penetrate tissue. The second member includes a mating surface engageable with the part and defining an inner cavity configured for disposal of the part. The part is telescopically movable relative to the second member to selectively translate the implant cavity relative to the second member.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system and related methods of use disclosed are discussed in terms of medical devices for the treatment of musculoskeletal disorders and more particularly, in terms of a spinal implant system including a bone fastener and a method for treating a spine. In some embodiments, the spinal implant system includes an implant comprising a bone fastener, such as, for example, a pedicle bone screw. In some embodiments, the spinal implant system includes an implant comprising an adjustable height bone screw that is employed with a method for manipulating a spine in connection with correction of deformities.

In some embodiments, the spinal implant system comprises an adjustable height pedicle screw. In some embodiments, the spinal implant system can be employed with a method to adjust a height of a pedicle screw while trying to seat a spinal rod with the pedicle screw. In some embodiments, the spinal implant system can be employed with a tulip or top loading system and avoids, resists and/or prevents bone screw pull out from an anatomy. In some embodiments, the spinal implant system comprises an adjustable height pedicle screw that provides the ability to stop or interrupt reduction and accommodates spinal rod position rather than the spinal rod being forced into a complete reduction or disposal in a home position.

In some embodiments, the spinal implant system comprises a pedicle screw including a spinal rod receiver, a screw shaft and a part, such as, for example, an attachment portion. In some embodiments, the screw shaft is driven into tissue via engagement of a hexagonal portion of the screw shaft. In some embodiments, the attachment portion can adjust up and down a selected distance, such as, for example, one or more millimeters (mm) in dorsal height. In some embodiments, a counter torque engagement of the hexagonal portion of the screw shaft can be employed to avoid, resist and/or prevent driving or pulling out of the bone screw from bone. In some embodiments, the attachment portion can be adjusted relative to a hexalobe feature of the screw shaft.

In some embodiments, the spinal implant system comprises a bone screw having a screw shaft with a transverse slot. In some embodiments, the bone screw avoids the adverse effects of micro-motion of its components. In some embodiments, the screw shaft includes inner female threads having a slit such that a compressive force can be applied to slightly deform the female threads. This deformation configuration creates an interference condition between mating threads of the attachment portion and the screw shaft to avoid, resist, prevent and/or eliminate micro-motion and reduce the effects of cyclic loading. In some embodiments, the screw shaft and/or attachment portion can include a friction element disposed between threaded surfaces to avoid, resist, prevent and/or eliminate micro-motion and reduce the effects of fatigue cyclic loading. In some embodiments, the screw shaft and/or attachment portion can include a polymer bushing that can absorb micro-motion. In some embodiments, the attachment portion includes a higher strength material relative to the bone screw, for example, high strength titanium or cobalt chromium.

In some embodiments, the spinal implant system comprises a bone screw including a part, such as, for example, a telescoping head and/or shaft that provides adjustable spinal rod seating with the bone screw. In some embodiments, the telescoping head and/or shaft, and screw shaft of the bone screw are expandable.

In some embodiments, the spinal implant system is employed with a method of treating a spine including correction and/or reduction maneuvers to apply reduction forces to seat a rod into a top loading or tulip head pedicle screw and/or connect a secure spinal construct with vertebrae. In some embodiments, the spinal implant system provides the flexibility to make adjustment to a spinal construct during a surgical procedure while resisting and/or preventing disengaging the pedicle screw from tissue. In some embodiments, the spinal implant system allows spinal construct adjustment while avoiding the need for rod bending, loss of bone-screw interface strength and/or bone screw pull out. In some embodiments, the spinal implant system allows spinal construct adjustment to screw height to accommodate rod position relative to vertebrae.

In some embodiments, the spinal implant system comprises a modular system that includes a bone fastener including an array of selectively coupled members, such as bone screw shafts and receivers. In some embodiments, the spinal implant system comprises a selectively coupled bone fastener that can be assembled on a surgical table or in-situ. In some embodiments, the selectively coupled bone fastener is assembled with a force of less than 50 Newtons (N). In some embodiments, the bone fastener is selectively coupled with a non-instrumented assembly. In some embodiments, the non-instrumented assembly comprises manually engaging a screw shaft with a body. In some embodiments, the non-instrumented assembly comprises manually engaging the screw shaft in a pop-on engagement with a body. In some embodiments, a force required to manually engage a screw shaft with a body in a non-instrumented assembly is in a range of 2 to 50 N. In some embodiments, a force required to manually engage a screw shaft with a body in a non-instrumented assembly is in a range of 5 to 10 N. In some embodiments, a screw shaft is manually engaged with a body in a non-instrumented assembly, as described herein, such that removal of a body from the screw shaft requires a force and/or a pull-out strength of at least 5000 N.

In some embodiments, the bone fastener is configured for assembly without the use of an instrument, such as, for example, a practitioner, surgeon and/or medical staff utilizes their hands for assembly. In some embodiments, the system requires minimal force to attach a body and a screw shaft assembly in-situ thereby reducing a pre-load on the vertebrae, such as, for, example, the pedicle.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a bone fastener, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-5, there are illustrated components of a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal implant, such as, for example, a bone fastener 170. In some embodiments, the components of spinal implant system 10 are configured to deliver and introduce components of one or more spinal constructs that include implants, such as, for example, receivers, spinal rods, connectors, plates and/or fasteners. The components of spinal implant system 10 include one or more components of a surgical treatment of tissue for positioning and alignment to stabilize a treated section of vertebrae. Bone fastener 170 comprises a member, such as, for example, an implant receiver 12 and a member, such as, for example, a screw shaft 14. Implant receiver 12 is connectable with screw shaft 14 by a part 16 to selectively adjust a distance of implant receiver 12 relative to tissue, as described herein. In some embodiments, the part 16 is relatively movable, for example, axially translatable relative to screw shaft 14 to adjust a height of an implant cavity of implant receiver 12 relative to vertebrae to accommodate position of a spinal rod for receipt thereof and/or in connection with reduction of a spinal rod with a receiver, as described herein. In some embodiments, screw shaft 14, part 16 and implant receiver 12 are assembled in situ or prior to implant to form bone fastener 170, as described herein.

Figure 1:
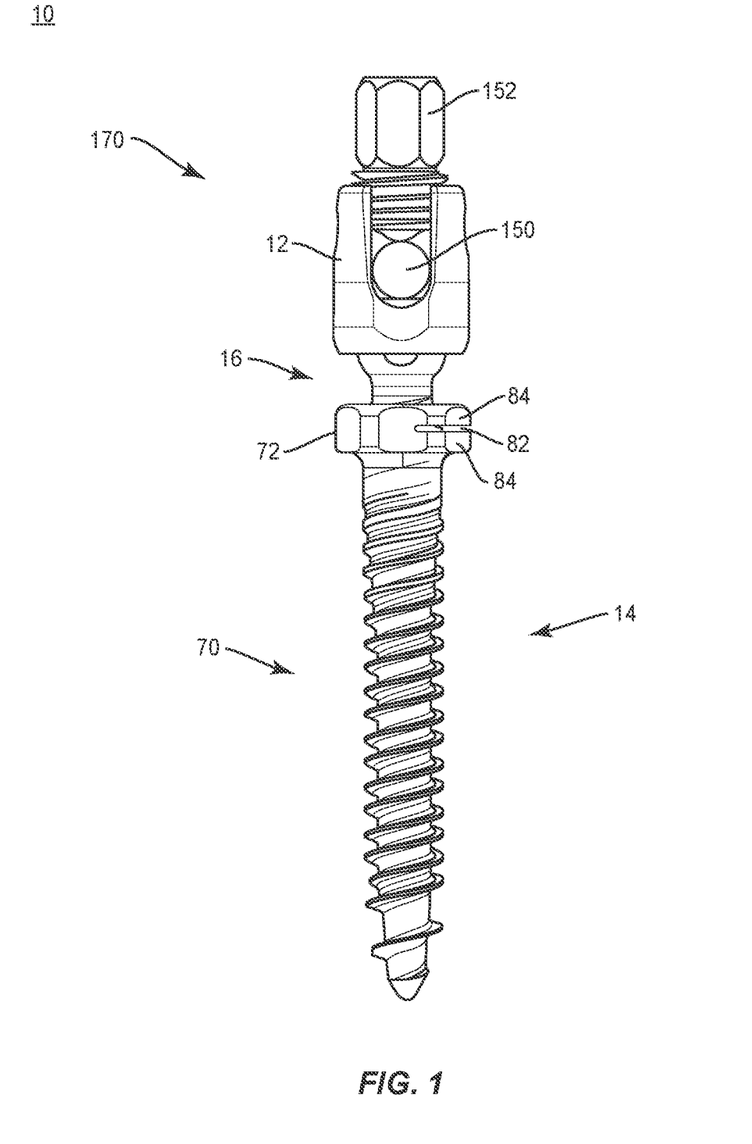
FIG. 1 is a side view of components of one embodiment of a spinal implant system in accordance with the principles of the present disclosure.
Figure 2:
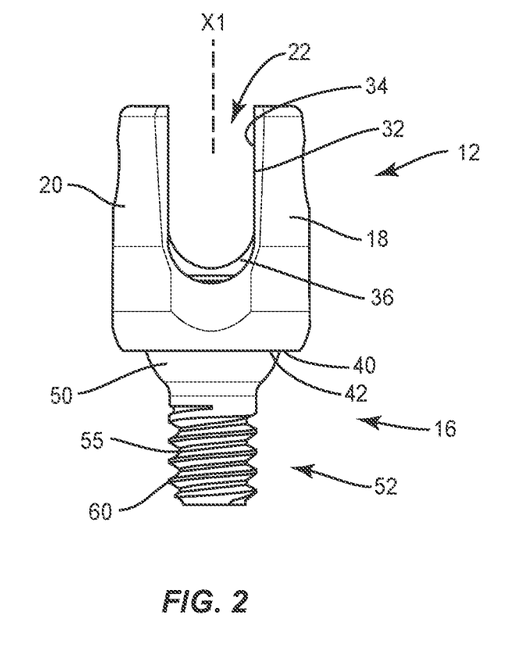
FIG. 2 is a side view of components of one embodiment of a spinal implant system in accordance with the principles of the present disclosure.
Figure 3:
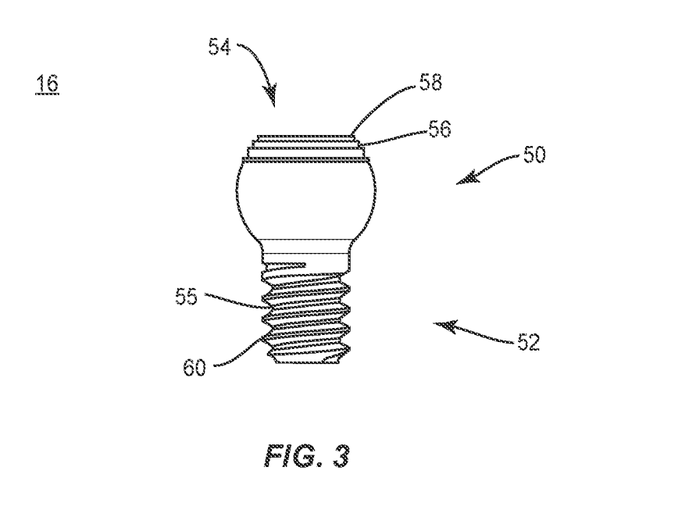
FIG. 3 is a side view of components of one embodiment of a spinal implant system in accordance with the principles of the present disclosure.

Implant receiver 12 extends along and defines an axis X1. Implant receiver 12 includes a pair of spaced apart arms 18, 20 that define an implant cavity 22 therebetween configured for disposal of a component of a spinal construct, such as, for example, a spinal rod 150. Arms 18, 20 each extend parallel to axis X1, as shown in FIG. 2. In some embodiments, arm 18 and/or arm 20 may be disposed at alternate orientations, relative to axis X1, such as, for example, transverse, perpendicular and/or other angular orientations such as acute or obtuse, coaxial and/or may be offset or staggered. Arms 18, 20 each include an arcuate outer surface extending between a pair of side surfaces. At least one of the outer surfaces and the side surfaces of arms 18, 20 have at least one recess or cavity therein configured to receive an insertion tool, compression instrument and/or instruments for inserting and tensioning bone fastener 170. In some embodiments, arms 18, 20 are connected at proximal and distal ends thereof such that implant receiver 12 defines a closed spinal rod slot.

Cavity 22 is substantially U-shaped. In some embodiments, all or only a portion of cavity 22 may have alternate cross section configurations, such as, for example, closed, V-shaped, W-shaped, oval, oblong triangular, square, polygonal, irregular, uniform, non-uniform, offset, staggered and/or tapered. Implant receiver 12 includes an inner surface 32. A portion of surface 32 includes a thread form 34 configured for engagement with a coupling member, such as, for example, a setscrew 152 to retain spinal rod 150 within cavity 22. In some embodiments, surface 32 may be disposed with the coupling member in alternate fixation configurations, such as, for example, friction fit, pressure fit, locking protrusion/recess, locking keyway and/or adhesive. In some embodiments, all or only a portion of surface 32 may have alternate surface configurations to enhance engagement with spinal rod 150 and/or setscrew 152, such as, for example, rough, arcuate, undulating, mesh, porous, semi-porous, dimpled and/or textured. In some embodiments, implant receiver 12 may include alternate configurations, such as, for example, closed, open and/or side access. In some embodiments, implant receiver 12 includes a crown 36 configured to facilitate positioning of spinal rod 150.

Implant receiver 12 includes a surface 40 that defines a cavity 42. Cavity 42 is configured for disposal of a head 50 of part 16, as described herein. In some embodiments, all or only a portion of surface 40 may have alternate surface configurations to enhance engagement with head 50, such as, for example, rough, arcuate, undulating, mesh, porous, semi-porous, dimpled and/or textured. In some embodiments, head 50 is engaged with surface 40 in a keyed connection. In some embodiments, head 50 is manually engageable with implant receiver 12 in a non-instrumented assembly, as described herein.

Part 16 includes head 50 and a shaft 52. Head 50 includes a tool socket 54 configured to engage a surgical tool or instrument. In some embodiments, socket 54 includes a hexagonal cross-section to facilitate engagement with a surgical tool or instrument, as described herein. In some embodiments, socket 54 may have alternative cross-sections, such as, for example, rectangular, polygonal, hexalobe, oval, or irregular. In some embodiments, head 50 includes a surface 56 that defines a plurality of ridges 58 to improve purchase of head 50 with implant receiver 12. Head 50 is configured for attachment with implant receiver 12, as described herein and shown in FIG. 2. In some embodiments, head 50 is translatable relative to screw shaft 14 in a telescoping configuration to facilitate translation of implant cavity 22 relative to tissue, as described herein.

Shaft 52 is configured for engagement with screw shaft 14. Shaft 52 includes an outer surface 55 having external threads 60. In some embodiments, threads 60 may include a single thread turn or a plurality of discrete threads. Shaft 52 is configured for a mating engagement with a threaded surface of screw shaft 14, as described herein. In some embodiments, part 16 is intra-operatively engageable to selectively translate implant cavity 22 relative to screw shaft 14.

Engagement of threads 60 with screw shaft 14 facilitates relative expansion of implant receiver 12 and screw shaft 14, as described herein. For example, engagement and rotation of part 16 causes implant receiver 12 to translate relative to screw shaft 14. In some embodiments, this configuration adjusts a dorsal height of implant cavity 22 relative to tissue, as described herein. In some embodiments, engagement of threads 60 with screw shaft 14 facilitates selective axial translation of part 16 and implant receiver 12 relative to screw shaft 14 to adjust a height of implant cavity 22 relative to vertebrae to accommodate position of a spinal rod for receipt thereof, as described herein. In some embodiments, the material of shaft 52 includes a material having a higher specific strength than the material of screw shaft 14. In some embodiments, a surgical instrument can be engaged with head 50 and/or implant receiver 12 to rotate head 50 and/or implant receiver 12 relative to screw shaft 14.

Figure 5:
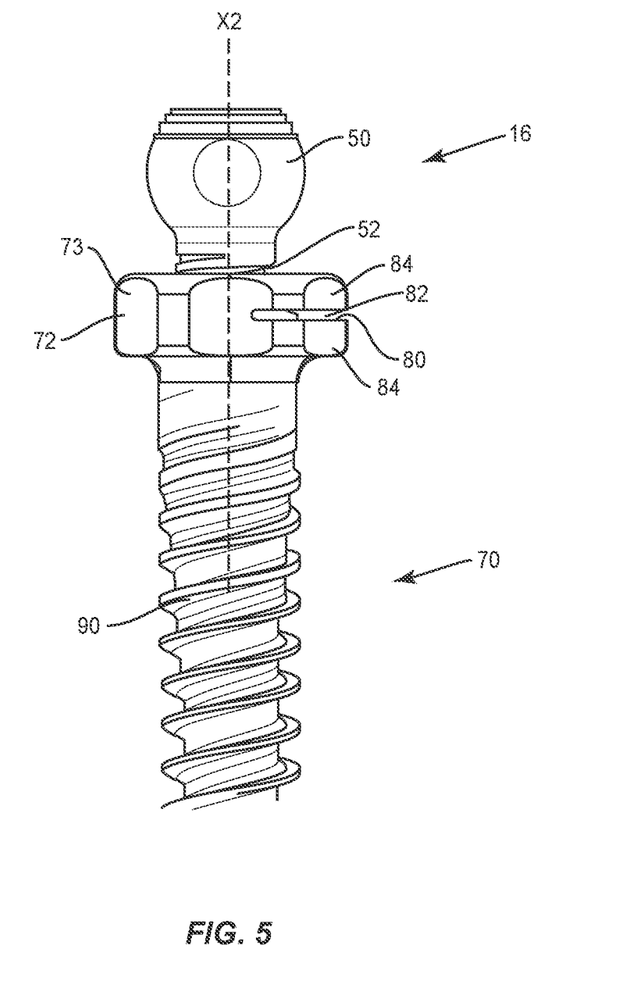
FIG. 5 is a break away view of the components shown in FIG. 4.
Figure 6:
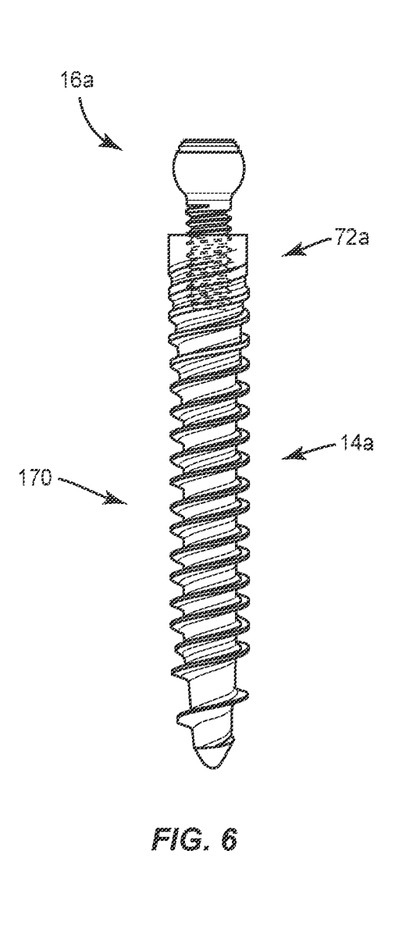
FIG. 6 is a side, cross section view of components of one embodiment of a spinal implant system in accordance with the principles of the present disclosure.
Figure 7:
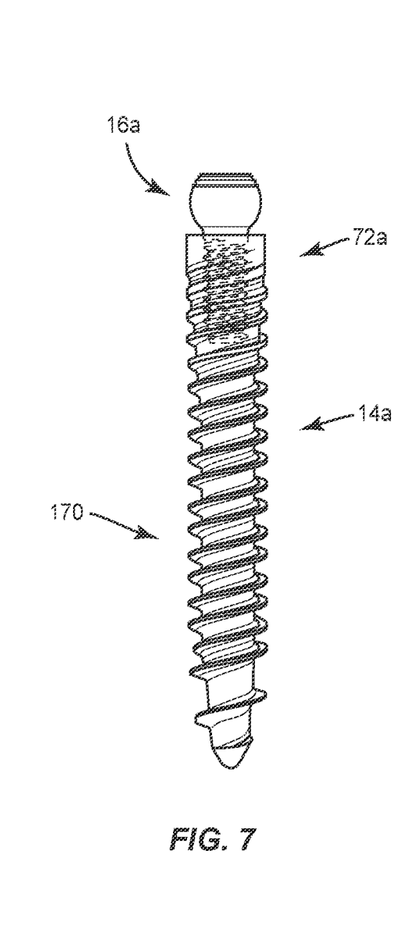
FIG. 7 is a side view of the components shown in FIG. 6.
Figure 8:
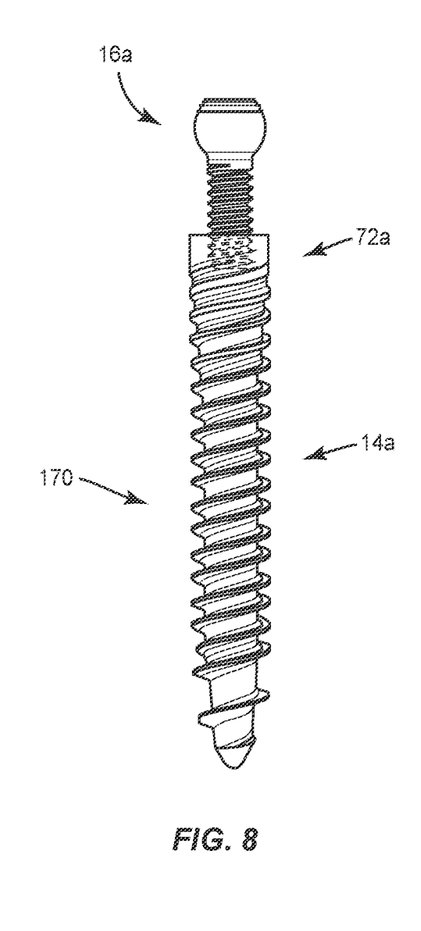
FIG. 8 is a side view of the components shown in FIG. 6.

Screw shaft 14 includes a body 70 and a head 72. Screw shaft 14 defines an axis X2. In some embodiments, head 72 includes an engagement surface, such as, for example, a flange 73. Flange 73 extends transverse to axis X2, as shown in FIG. 5. In some embodiments, flange 73 may be disposed at alternate orientations relative to axis X2, such as, for example, perpendicular and/or other angular orientations such as acute or obtuse, coaxial and/or may be offset or staggered. In some embodiments, flange 73 may include various configurations, such as, for example, hexalobe, rectangular, polygonal, oval, or irregular. Flange 73 is configured for engagement with a surgical instrument, such as, for example, a wrench. For example, the wrench is engageable with flange 73 to provide a counter torque as part 16 is rotated. Engagement of the wrench with flange 73 as a counter torque resists and/or prevents screw shaft 14 from rotating and engaging and/or disengaging from tissue such as pull out during rotation of part 16 relative to screw shaft 14, as described herein. In one embodiment, as shown in FIG. 6, bone fastener 170 includes a screw shaft 14a, similar to screw shaft 14, having a head 72a of uniform diameter, which is engageable with a part 16a, similar to part 16, for translation relative to screw shaft 14a between a contracted orientation, as shown in FIG. 7, and an expanded orientation, as shown in FIG. 8, to adjust a height of implant cavity 22 relative to vertebrae to accommodate position of a spinal rod for receipt thereof, as described herein.

Figure 4:
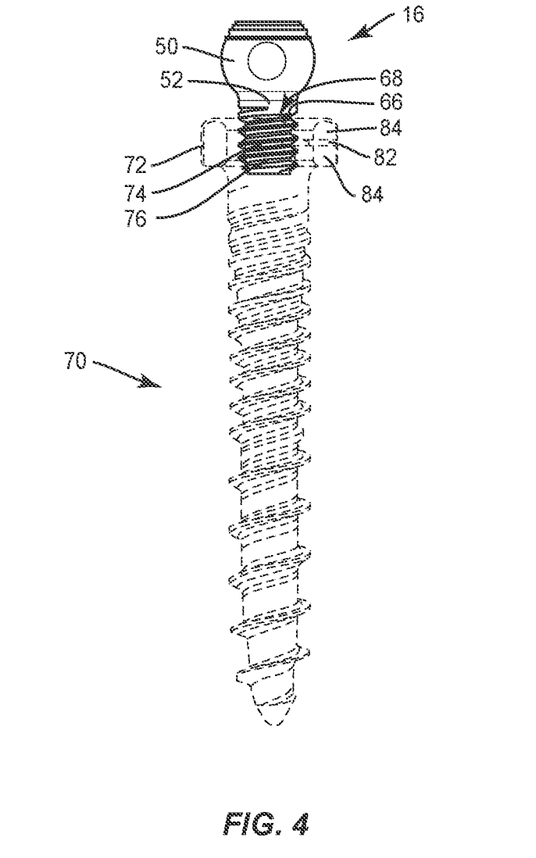
FIG. 4 is a side view, in part phantom, of the components of one embodiment of a spinal implant system in accordance with the principles of the present disclosure.
Figure 9:
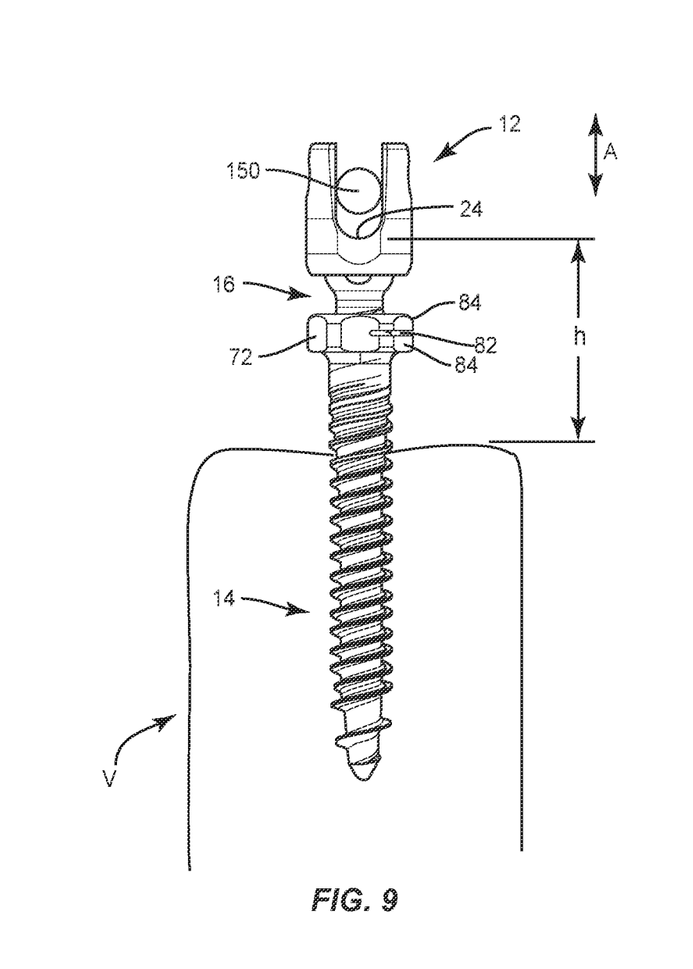
FIG. 9 is a perspective view of components of one embodiment of a spinal implant system in accordance with the principles of the present disclosure disposed with vertebrae.
Figure 10:
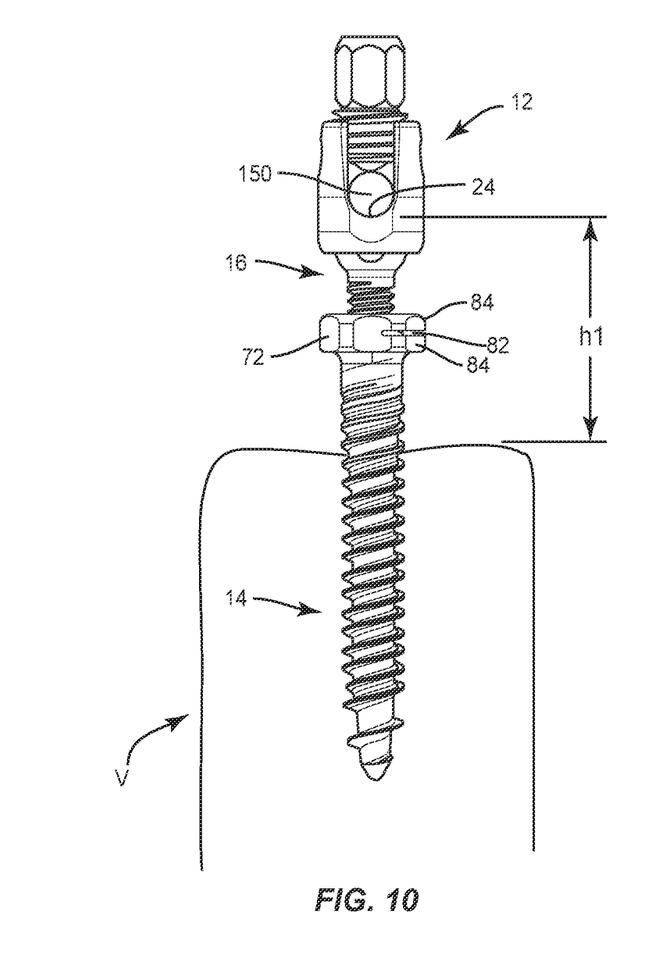
FIG. 10 is a perspective view of components of one embodiment of a spinal implant system in accordance with the principles of the present disclosure disposed with vertebrae.

Head 72 includes a surface 66 that defines a cavity 68. Cavity 68 is configured for moveable disposal of shaft 52, as shown in FIG. 4. Cavity 68 includes a mating surface 74 having threads 76. Threads 76 are configured for a mating engagement with threads 60. Engagement of threads 76, 60 facilitates relative translation of implant receiver 12 and screw shaft 14 between a contracted orientation, as shown in FIG. 9, and an expanded orientation, as shown in FIG. 10.

For example, spinal rod 150 is disposable with implant cavity 22 for reduction with implant receiver 12 such that spinal rod 150 is spaced apart and defines a gap with an inner surface 24 of implant receiver 12, which may include crown 36. The height of implant cavity 22 can be adjusted, as described herein, relative to vertebrae to accommodate position of spinal rod 150 for receipt thereof. A surgical driver is engageable with socket 54 of part 16 for rotation thereof to facilitate engagement of threads 76, 60 such that part 16 and implant receiver 12 connected therewith axially translate, in a direction shown by arrows A in FIG. 9, relative to screw shaft 14.

Part 16 is rotatable in a clockwise orientation such that part 16 is drawn into cavity 68, and implant receiver 12 and screw shaft 14 contract. Part 16 is rotatable clockwise such that surface 24 is translatable relative to vertebrae V, as shown in FIG. 9, to adjust a distance of implant cavity 22 and surface 24 relative to vertebrae V to a distance, such as, for example, a height h. Part 16 is rotatable in a counter-clockwise orientation such that part 16 extends from cavity 68 and implant receiver 12 and screw shaft 14 expand. Part 16 is rotatable counter-clockwise such that surface 24 is translatable relative to vertebrae V, as shown in FIG. 10, to adjust a distance of implant cavity 22 and surface 24 relative to vertebrae V to a distance, such as, for example, a height h1. Translation of implant cavity 22 and surface 24 relative to vertebrae V facilitates adjustment of implant receiver 12 for reduction of spinal rod 150. In some embodiments, a surgical driver is engageable with socket 54 to adjust the height of implant receiver 12, pre-operatively or intra-operatively, and spinal rod 150 can be manipulated, moved or removed from implant cavity 22 for intra-operative height adjustment. In some embodiments, height h is a minimum distance and height h1 is a maximum distance. In some embodiments, implant cavity 22 and surface 24 are translatable relative to vertebrae V in range of distance between height h and height h1.

Head 72 includes a surface 80 of flange 73 that defines a transverse slot 82. Collars 84 are compressed or forced together during manufacturing such that slot 82 is closed. This creates a permanently deformed thread 76. As part 16 is inserted into screw shaft 14, threads 60 engage with threads 76. The interference between the threads reduce the effects of cyclic loading on implant receiver 12, part 16 and/or screw shaft. In some embodiments, this configuration reduces the effects of cyclic loading on implant receiver 12, part 16 and/or screw shaft 14. In some embodiments, screw shaft 14 and/or part 16 can include a friction element disposed between threads 76, 60 to avoid, resist, prevent and/or eliminate micro-motion and reduce the effects of cyclic loading. In some embodiments, the friction element includes a polymer bushing, lock nut and/or lock washer to distribute a load applied to the components of bone fastener 170. In some embodiments, the polymer bushing, lock nut and/or lock washer resists and/or prevents loosening of the components of bone fastener 170 under vibrations and torque. In some embodiments, the polymer bushing, a portion of the lock nut and/or a portion of the lock washer elastically or plastically deforms to provide locking. In some embodiments, the lock nut and/or lock washer includes a polymer bushing.

Body 70 includes a shaft 90 configured to penetrate tissue, such as, for example, bone. In some embodiments, shaft 90 includes an outer surface having an external thread form. In some embodiments, the external thread form may include a single thread turn or a plurality of discrete threads.

Figure 11:
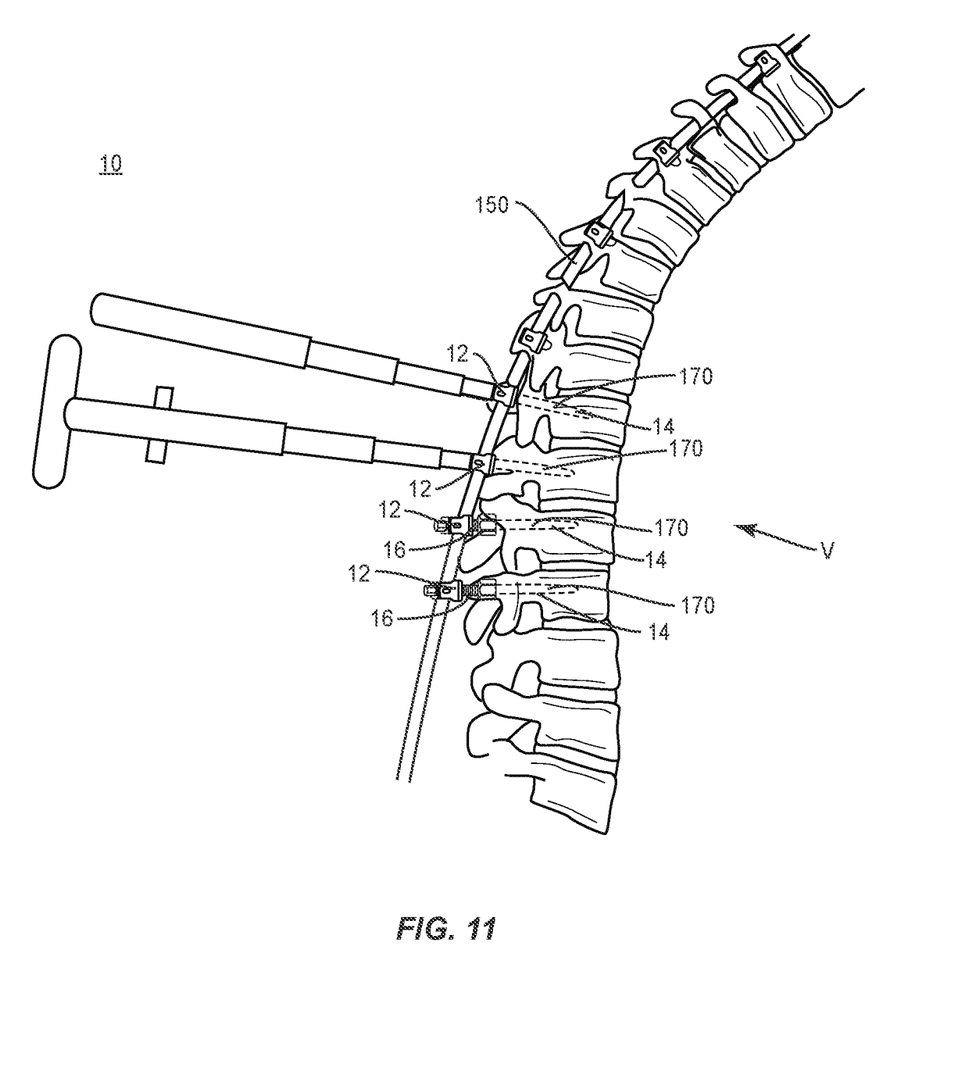
FIG. 11 is a perspective view of components of one embodiment of a spinal implant system in accordance with the principles of the present disclosure disposed with vertebrae.

In assembly, operation and use, spinal implant system 10, similar to the systems and methods described herein, is employed with a surgical procedure for treating disorders of the spine, such as those described herein, as shown in FIGS. 9-11. In some embodiments, one or all of the components of spinal implant system 10 can be delivered as a pre-assembled device or can be assembled in situ.

A surgical treatment including spinal implant system 10 can be used for correction and alignment in stabilization of a treated section of vertebrae V. In an exemplary use, a medical practitioner obtains access to a surgical site including vertebrae V via a posterior surgical approach. In some embodiments, the surgical site may be accessed in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area.

An incision is made in the body of a patient and a cutting instrument (not shown) creates a surgical pathway for delivery and implantation of components of spinal implant system 10 with vertebrae V. A preparation instrument (not shown) can be employed to prepare tissue surfaces of vertebrae V, as well as for aspiration and irrigation of a surgical region.

Spinal implant system 10 includes bone fasteners 170, as described herein, which are delivered to the surgical site for disposal with vertebrae V in connection with the surgical procedure. In some embodiments, one or more bone fasteners 170 are disposed with vertebrae V in alternate orientations relative to each other, such as, for example, parallel, series, perpendicular, adjacent, co-axial, co-planar, arcuate, offset, staggered, transverse, angular and/or relative posterior/anterior orientations and/or at alternate vertebral levels.

A surgical tool or driver is engageable with socket 54 of part 16 for rotation thereof to facilitate engagement of threads 76, 60 and connection of part 16 with screw shaft 14, as described herein. Implant receiver 12 is engaged with head 50 of part 16 for assembly of the components of bone fastener 170, as described herein. In some embodiments, the components of bone fastener 170 can be pre-operatively or intra-operatively connected and/or assembled. In some embodiments, screw shaft 14 can be connected with tissue and part 16 and/or implant receiver 12 intra-operatively connected and/or assembled therewith. In some embodiments, bone fastener 170 is assembled in a non-instrumented assembly on a back table of an operating room during a surgical procedure, as described herein. In some embodiments, bone fastener 170 is assembled in an instrumented assembly.

Pilot holes are made in vertebrae V in a selected orientation. A part 16 is connected with one or more screw shafts 14, and shafts 90 are aligned with the pilot holes to fasten one or more bone fasteners 170 with the tissue of vertebrae V. Implant receiver 12 is engaged with head 50 for assembly of bone fasteners 170, as described herein.

For example, pre-operatively or intra-operatively, part 16 is rotatable in a clockwise orientation, as described herein, such that implant cavity 22 and surface 24 are disposed a height h relative to vertebrae V, as shown in FIG. 9. Spinal rod 150 is shaped, contoured and/or bent to a selected configuration for a selected curvature or final lordosis of vertebrae V as attached with bone fasteners 170 in connection with the surgical procedure. Spinal rod 150 is delivered to the surgical site and oriented for alignment with implant cavities 22 of bone fasteners 170. Reduction instruments are connected with bone fasteners 170 to reduce spinal rod 150 with implant cavities 22.

The reduction instruments manipulate each of bone fasteners 170. For example, spinal rod 150 is disposable with implant cavities 22 for reduction with implant receivers 12, however, spinal rod 150 may not fully seat within one or more implant cavities 22, as shown in FIG. 9, due to the selected shape, contour and/or bend of spinal rod 150. Spinal rod 150 is spaced apart and defines a gap with inner surface 24, which may include crown 36. The height of implant cavity 22 can be adjusted, as described herein, relative to vertebrae V to accommodate position of spinal rod 150. A surgical driver is engageable with socket 54 of part 16 for rotation thereof to facilitate engagement of threads 76, 60 such that part 16 and implant receiver 12 connected therewith axially translate, in a direction shown by arrows A in FIG. 9, relative to screw shaft 14. In some embodiments, a surgical driver is engageable with socket 54 to adjust the height of implant receiver 12, pre-operatively or intra-operatively, and spinal rod 150 can be manipulated, moved or removed from implant cavity 22 for intra-operative height adjustment.

A surgical instrument, such as, for example, a crowfoot wrench (not shown) is engageable with flange 73 as a counter torque to resist and/or prevent screw shaft 14 from rotating, engaging and/or disengaging from tissue such as pull out during rotation of part 16 relative to screw shaft 14, as described herein. A surgical driver is engageable with socket 54 and part 16 is rotatable counter-clockwise such that surface 24 is translatable relative to vertebrae V, as shown in FIG. 10, to adjust a distance of implant cavity 22 and surface 24 relative to vertebrae V to a height h1. Translation of implant cavity 22 and surface 24 relative to vertebrae V facilitates adjustment of implant receiver 12, as described herein, for reduction of spinal rod 150. In some embodiments, this configuration allows adjustment of bone fastener 170 for reduction of spinal rod 150 therewith while avoiding the need for rod bending, loss of bone-screw interface strength and/or bone screw pull out. In some embodiments collars 84 are compressed or forced together during manufacturing such that slot 82 is closed. This creates a permanently deformed thread 76. As part 16 is inserted into screw shaft 14, threads 60 engage with threads 76. The interference between the threads reduce the effects of cyclic loading on implant receiver 12, part 16 and/or screw shaft 14. Set screws 152 are engaged with bone fasteners 170 to finally tighten spinal rod 150 for fixation with vertebrae V.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

In some embodiments, spinal implant system 10 can include one or a plurality of bone fasteners 170 described herein and/or fixation elements, which may be employed with a single vertebral level or a plurality of vertebral levels. In some embodiments, bone fasteners 170 may be engaged with vertebrae in various orientations, such as, for example, series, parallel, offset, staggered and/or alternate vertebral levels. In some embodiments, bone fasteners 170 may be configured as multi-axial screws, sagittal angulation screws, pedicle screws, mono-axial screws, uni-planar screws, fixed screws, anchors, tissue penetrating screws, conventional screws, expanding screws. In some embodiments, bone fasteners 170 may be employed with wedges, anchors, buttons, clips, snaps, friction fittings, compressive fittings, expanding rivets, staples, nails, adhesives, posts, connectors, fixation plates and/or post.

Upon completion of the procedure, the non-implanted components, surgical instruments and assemblies of spinal implant system 10 are removed and the incision is closed. In some embodiments, the use of microsurgical and image guided technologies may be employed to access, view and repair spinal deterioration or damage, with the aid of spinal implant system 10. The components of spinal implant system 10 can be made of radiolucent materials such as polymers. Radiomarkers may be included for identification under x-ray, fluoroscopy, CT or other imaging techniques.

In one embodiment, as shown in FIGS. 12-15, spinal implant system 10, similar to the systems and methods described herein, includes bone fasteners 270, similar to bone fastener 170 described herein. Bone fastener 270 comprises an implant receiver 312, similar to implant receiver 12 described herein, and screw shaft 14 described herein. Implant receiver 312 is connectable with screw shaft 14 by a part 316, similar to part 16 described herein, to selectively adjust a distance of implant receiver 312 relative to tissue, as described herein.

Implant receiver 312 includes a pair of spaced apart arms 318, 320 that define an implant cavity 322 therebetween configured for disposal of spinal rod 150. Implant receiver 312 includes a crown 336 configured to facilitate positioning of spinal rod 150. Implant receiver 312 includes a surface 340 that defines a cavity 342. Cavity 342 is configured for disposal of a base 400 of part 316 in a non-instrumented assembly, as described herein.

Part 316 includes a head 350 and a shaft 352. Head 350 includes a socket 354 configured to engage a surgical tool or instrument. Head 350 is configured for connection with base 400. Base 400 includes a wall 402, which has a surface 404 that defines a cavity 406 configured for disposal of head 350. Surface 404 facilitates engagement of head 350 with base 400 via a pressure and/or force fit connection. In some embodiments, surface 404 facilitates a non-instrumented assembly with base 400 and head 350 via an expandable ring. In some embodiments, base 400 may be disposed with head 350 in alternate fixation configurations, such as, for example, friction fit, pressure fit, locking protrusion/recess, locking keyway and/or adhesive.

Figure 12:
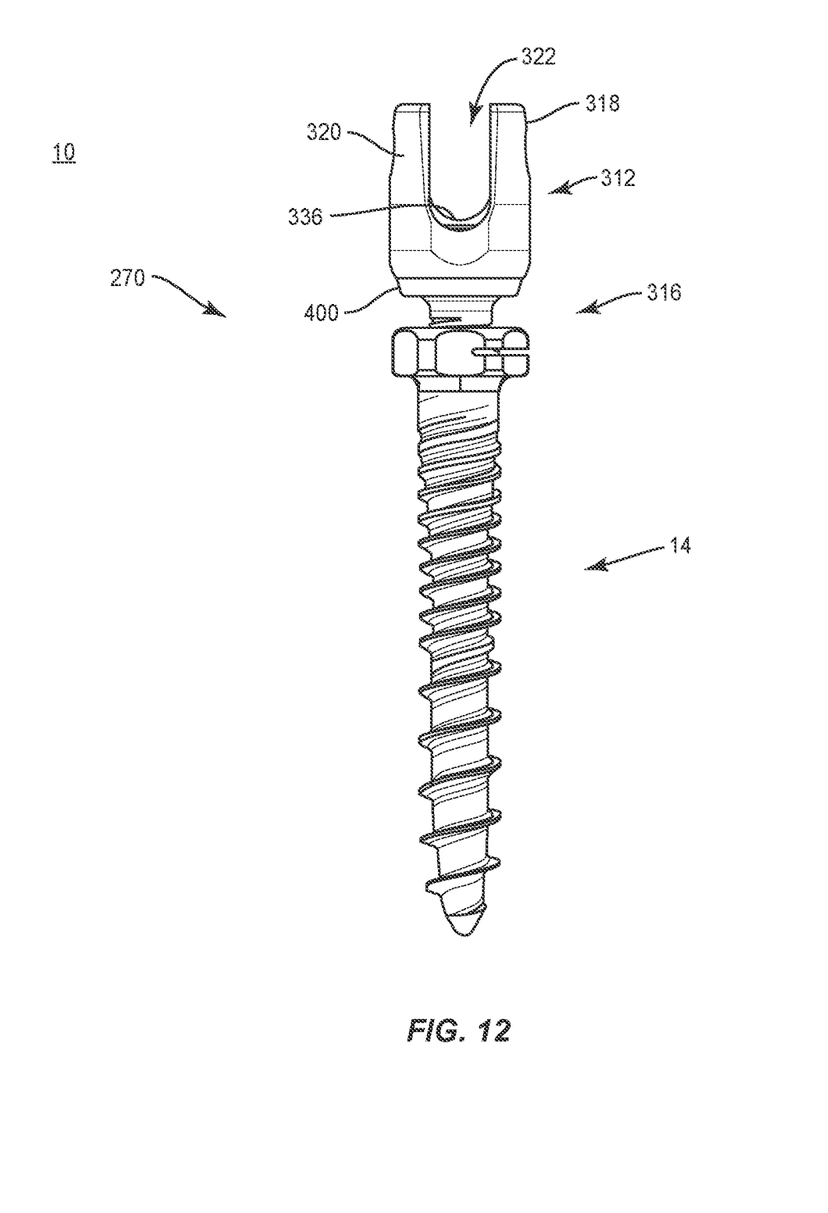
FIG. 12 is a side view of components of one embodiment of a spinal implant system in accordance with the principles of the present disclosure.
Figure 13:
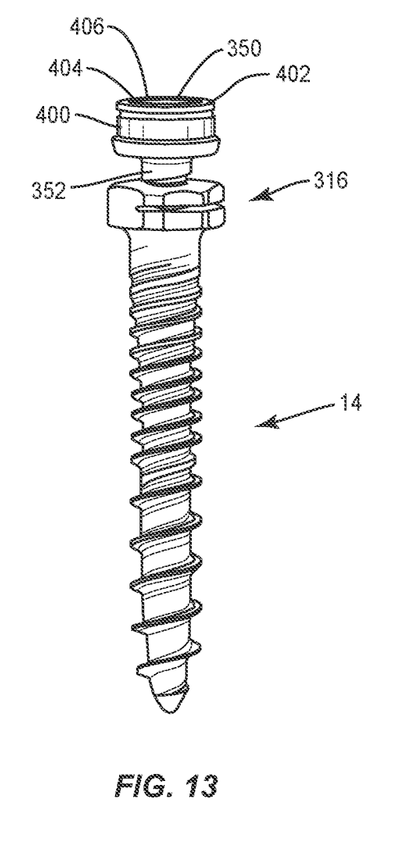
FIG. 13 is a perspective view of components of one embodiment of a spinal implant system in accordance with the principles of the present disclosure.
Figure 14:
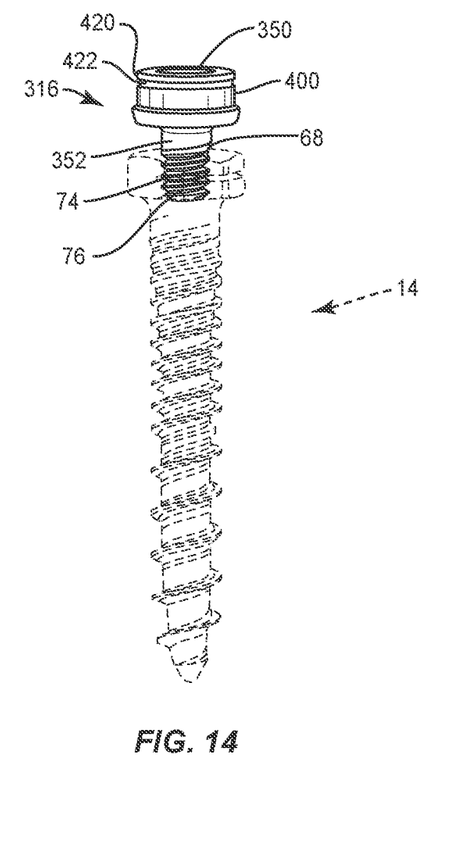
FIG. 14 is a perspective view, in part phantom, of the components shown in FIG. 13.
Figure 15:
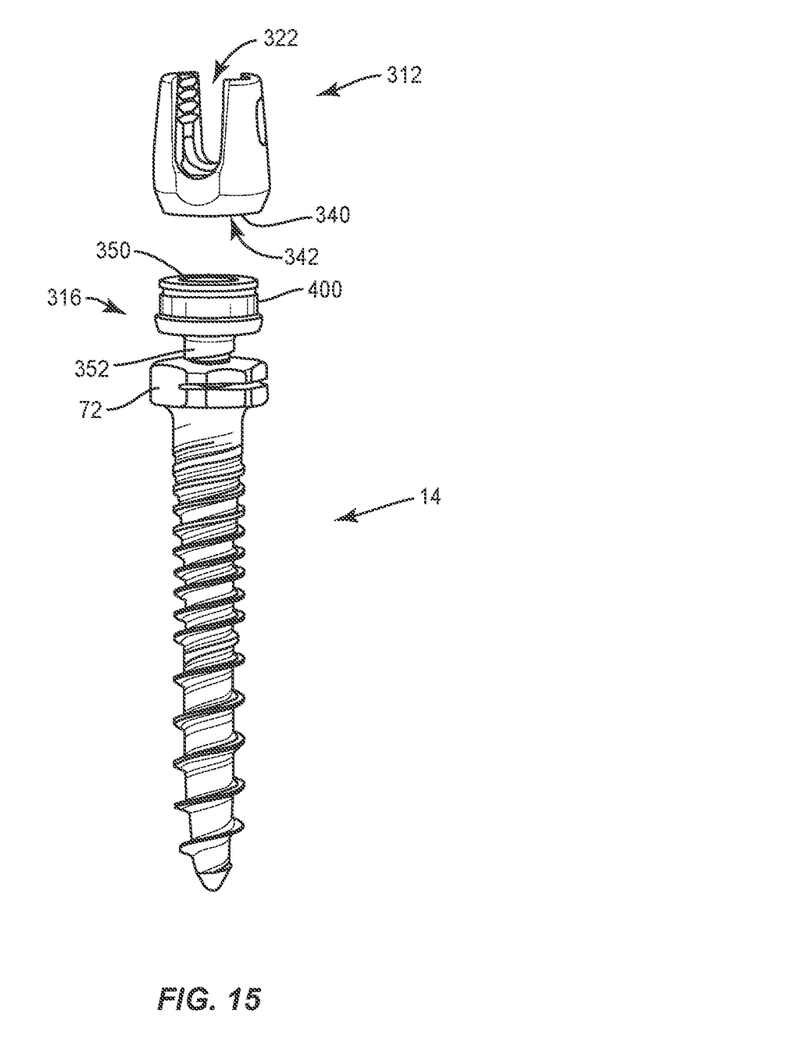
FIG. 15 is a perspective view of the components shown in FIG. 12 with parts separated.

Wall 402 includes a surface 420 that defines a cavity, such as, for example, a groove 422. Groove 422 is configured for disposal of a ring (not shown) to prevent displacement of the ring from a channel disposed with implant receiver 312 and to permanently fix part 316 with implant receiver 312, as shown in FIG. 12. For example, base 400 is assembled with head 350. The base 400/part 316 assembly is connected with implant receiver 312 such that the ring resiliently contracts to a capture orientation to permanently assemble part 316 with implant receiver 312.

In some embodiments, spinal implant system 10 comprises a modular system that includes bone fastener 270 including an array of selectively coupled members, such as implant receivers 312 and screw shafts 14. In some embodiments, spinal implant system 10 comprises a selectively coupled bone fastener 270 that can be assembled on a surgical table or in-situ. In some embodiments, the base 400/part 316 assembly is manually engageable with implant receiver 312 in a non-instrumented assembly, as described herein. In some embodiments, manual engagement and/or non-instrumented assembly of the base 400/part 316 assembly with implant receiver 312 includes coupling without use of separate and/or independent instrumentation to effect assembly.

In some embodiments, manual engagement and/or non-instrumented assembly includes a practitioner, surgeon and/or medical staff grasping the base 400/part 316 assembly and implant receiver 312 and forcibly assembling the components. In some embodiments, manual engagement and/or non-instrumented assembly includes a practitioner, surgeon and/or medical staff grasping the base 400/part 316 assembly and implant receiver 312 and forcibly snap fitting the components together, as described herein. In some embodiments, manual engagement and/or non-instrumented assembly includes a practitioner, surgeon and/or medical staff grasping the base 400/part 316 assembly and implant receiver 312 and forcibly pop fitting the components together, as described herein. In some embodiments, a force in a range of 2-50 N is required to manually assemble the base 400/part 316 assembly with implant receiver 312 and forcibly assemble the components. For example, a force in a range of 2-50 N is required to snap fit and/or pop fit assemble the base 400/part 316 assembly with implant receiver 312. In some embodiments, a force in a range of 5-10 N is required to manually engage the base 400/part 316 assembly with implant receiver 312 and forcibly assemble the components. For example, a force in a range of 5-10 N is required to snap fit and/or pop fit the base 400/part 316 assembly with implant receiver 312. In some embodiments, the base 400/part 316 assembly is manually engaged with implant receiver 312 in a non-instrumented assembly, as described herein, such that removal of the base 400/part 316 assembly and implant receiver 312 requires a force and/or a pull-out strength of at least 5000 N. In some embodiments, this configuration provides manually engageable components that are assembled without instrumentation, and subsequent to assembly, the assembled components have a selected pull-out strength and/or can be pulled apart, removed and/or separated with a minimum required force.

Shaft 352 is configured for engagement with mating surface 74 of screw shaft 14, as described herein. Part 316 is pre-operatively or intra-operatively engageable to selectively translate implant cavity 322 relative to screw shaft 14, similar to that described herein. For example, rotation of part 316 causes implant receiver 312 to translate for adjustment of a dorsal height of implant cavity 322 relative to tissue.

In some embodiments, spinal implant system 10 comprises a spinal implant kit, as described herein, which includes a plurality of implant receivers 312, parts 316 and/or screw shafts 14. In some embodiments, implant receiver 312 and/or part 316 can be selected from the plurality of implant receivers and/or parts such that implant receiver 312 and/or part 316 are connectable with an interchangeable member, such as, for example, a screw shaft 14.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone fastener comprising:
    a first member defining an implant cavity and a bore extending through a distal end of the first member;
    a second member comprising a proximal portion and a distal portion configured to penetrate tissue, the proximal portion including a threaded inner surface defining an opening, the proximal portion defining a transverse slot; and
    a third member comprising a head configured for disposal within the bore and threaded shaft configured for engagement with the threaded inner surface to selectively translate the implant cavity relative to the second member, the head having a maximum diameter less than a maximum diameter of the bore.

2. A bone fastener as recited in claim 1, wherein the third member is intra-operatively engageable to selectively translate the implant cavity relative to the second member.

3. A bone fastener as recited in claim 1, wherein the third member is engageable to adjust a dorsal height of the implant cavity relative to the tissue.

4. A bone fastener as recited in claim 1, wherein the third member is engageable such that the members are expandable to adjust position of the implant cavity relative to the tissue.

5. A bone fastener as recited in claim 1, wherein the threaded inner surface includes a first thread and a second thread, at least a portion of the second thread being spaced apart from at least a portion of the first thread by a transverse slot.

6. A bone fastener as recited in claim 1, wherein the threaded inner surface includes deformable threads.

7. A bone fastener as recited in claim 1, wherein the proximal portion includes a flange, the flange comprising a plurality of flats configured for engagement with a surgical instrument.

8. A bone fastener as recited in claim 1, further comprising a friction element disposed between the threaded shaft and the threaded inner surface.

9. A bone fastener as recited in claim 8, wherein the friction element includes a polymer bushing.

10. A bone fastener as recited in claim 1, further comprising a polymer lock washer disposed between the threaded shaft and the threaded inner surface.

11. A bone fastener as recited in claim 1, wherein the head includes a tool socket disposed in alignment with the implant cavity.

12. A bone fastener as recited in claim 1, wherein the third member includes a material having a higher specific strength than the second member.

13. A bone fastener as recited in claim 1, wherein the first member and the third member are engageable in a snap-fit assembly.

14. A bone fastener as recited in claim 1, wherein the third member is manually engageable with the first member to connect the third member and the first member in a non-instrumented assembly.

15. A bone fastener as recited in claim 1, wherein the head is configured to be bottom loaded into the bore.

16. A bone fastener comprising:
    a receiver including spaced apart arms defining an implant cavity therebetween, the receiver defining a bore extending through a distal end of the first member, the bore being in communication with the implant cavity;
    a screw comprising a proximal portion and a distal portion configured to penetrate tissue, the proximal portion having threaded inner surface defining a throughhole; and
    a connector comprising a head configured for disposal within the bore and threaded shaft configured for engagement with the threaded inner surface to selectively translate the receiver relative to the screw, the head having a maximum diameter less than a maximum diameter of the bore,
    wherein the proximal portion includes a flange having the threaded inner surface, the flange comprising an opposite outer surface comprising a plurality of flats configured for engagement with a wrench, the flange defining a maximum diameter of the screw, the flange comprising a first section and a second section, a portion of the first section being spaced apart from a portion of the second section by a transverse slot that interrupts a thread of the threaded inner surface.

17. A bone fastener as recited in claim 16, wherein the proximal portion has a uniform diameter between a proximal end surface of the proximal portion and a threaded outer surface of the distal portion.

18. A bone fastener comprising:
    a first member defining an implant cavity and a bore extending through a distal end of the first member;
    a second member comprising a proximal portion and a distal portion configured to penetrate tissue, the proximal portion including a threaded inner surface defining an opening;
    a third member comprising a head configured for disposal within the bore and threaded shaft configured for engagement with the threaded inner surface to selectively translate the implant cavity relative to the second member, the head having a maximum diameter less than a maximum diameter of the bore; and a friction element disposed between the threaded shaft and the threaded inner surface.

* * * * *